(12) United States Patent
Hupke et al.

(10) Patent No.: US 8,498,878 B2
(45) Date of Patent: Jul. 30, 2013

(54) INTELLIGENT MEDICAL CHART CAPTURE SYSTEM

(75) Inventors: Carlton Hupke, Sioux Falls, SD (US); Marvin Addink, Sioux Falls, SD (US)

(73) Assignee: EDCO Group Inc., St. Louis, MO (US)

( * ) Notice: Subject to any disclaimer, the term of this patent is extended or adjusted under 35 U.S.C. 154(b) by 1305 days.

(21) Appl. No.: 11/544,829

(22) Filed: Oct. 6, 2006

(65) Prior Publication Data

US 2009/0063189 A1 Mar. 5, 2009

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC ............................................... 705/2, 3
See application file for complete search history.

(56) References Cited

U.S. PATENT DOCUMENTS

| | | | | |
|---|---|---|---|---|
| 5,052,043 | A * | 9/1991 | Gaborski | 382/157 |
| 2002/0169638 | A1 * | 11/2002 | Rodriguez-Cue | 705/3 |
| 2004/0162831 | A1 * | 8/2004 | Patterson | 707/100 |
| 2004/0255252 | A1 * | 12/2004 | Rodriguez et al. | 715/762 |
| 2005/0024679 | A1 * | 2/2005 | Yoda et al. | 358/1.15 |

\* cited by examiner

*Primary Examiner* — Neha Patel
(74) *Attorney, Agent, or Firm* — Woodard, Emhardt, Moriarty, McNett & Henry LLP

(57) ABSTRACT

A method of capturing and processing medical charts of a health care facility includes building a document capture template for types of documents used by the health care facility, forming a batch of medical charts including at least one medical chart that includes at least one document comprising at least one page. The pages of the medical chart are undivided from each other. The method includes scanning the pages of the batch of medical charts, recognizing characters of text marked on the pages of the medical charts, analyzing the text of the pages of the medical charts using the document capture template, dividing the scanned pages into at least two documents, assigning a document type to each of the at least two documents, and creating an index of the pages using the document types assigned to each of the at least two documents.

6 Claims, 12 Drawing Sheets

INTELLIGENT MEDICAL CHART CAPTURE SYSTEM

BACKGROUND OF THE INVENTION

1. Field of the Invention

The present invention relates to document scanning and retention systems and more particularly pertains to a new intelligent medical chart capture system for scanning medical charts and discriminating between the size and type of documents in the medical chart without needing to manually separate and classify by type the documents in the chart.

2. Description of the Prior Art

The Health Insurance Portability and Accountability Act (HIPAA) of 1996 and similar privacy initiatives in Canada require hospitals and other health care organizations to effectively protect certain health data of their patients. Handling and accessing this health data in a paper-based format is labor intensive and inefficient. Protecting the health data in the paper-based format is also difficult to ensure that access is provided only to authorized personnel. These initiatives have dramatically changed the focus of medical records management in hospitals to finding methods for storing, retrieving and tracking access to data efficiently and effectively.

In addition, financial challenges to hospitals include pressure to contain or reduce costs and administrative space in favor of strategies and initiatives for improving health care. As a result, space in health care facilities is more valuable for patient care than medical record handling and storage. Storage of growing paper medical records poses challenges to Medical Record/Health Information Management departments to retain patient medical charts in a way that the chart can be quickly retrieved for medical care or patient review, while maintaining order in the handling of the records for billing purposes and ensuring chart completeness.

As hospitals strive to enhance patient care with electronic clinical care systems and systems that provide test data and results, managing paper charts has and will become increasingly difficult. The pressure to put into electronic form the medical forms and test results that currently remain available only in paper form (and thus as a paper portion of a patient's medical chart) increases as portals and integration among health care systems attempt to strengthen the usability and availability of the records.

The inhibiting factors to electronically capturing paper records efficiently for most hospitals include finding an efficient method in electronic systems for classifying forms of a medical chart as different document types, and managing access to the medical chart during the scanning process. The documents in medical charts are highly diverse, depending in part upon the type of visit (e.g., emergency room visit, scheduled appointment), the reason for the visit (e.g., type of injury, type of diagnosis), the department or departments of the healthcare facility visited by the patent, the types of health care services performed, etc. FIG. 1 of the drawings is illustrative of the variety in the makeup of a medical chart, with a chart including one or more documents and the documents including one or more pages, and the occasional loose document that is not a complete chart for a patient. More significantly, the variety of forms or papers that may make up each document of a patient chart can be enormous, especially in a hospital health care facility where there may be hundreds of different services provided and recorded in the chart. This significant variety in the form and content of each chart makes it exceedingly difficult to automatically determine the size (i.e., number of pages) of the documents in the chart and also discriminate between the type of documents in the chart being captured, and then electronically mark the separated documents and accurately identify the content for indexing and future retrieval.

Still further complicating any attempt to electronically capture and process medical charts in an automatic manner is the fact that the documents or forms used in one health care facility will typically vary significantly from documents used in other health care facilities, which makes it difficult to apply one solution across more than one health care facility. Yet another challenge to electronic capture is that the types of documents used will change over time, with some document types being added and some being eliminated. Further, the form and content of the documents within a document type will tend to change as variations are made and old forms are replaced by new forms.

One approach that has been attempted is to apply different bar codes to the different types of documents in a medical chart in order to facilitate document discrimination when scanning. However, the application, or integration, of bar codes to documents of a health care facility may require the changeover of the forms used in the facility. The expense associated with changing forms throughout a hospital or heath care facility can be very significant. The changeover process typically requires the printing of the new bar coded forms, distribution of the new forms, destruction of all non-bar coded forms, and retraining the personnel using the new bar coded forms. The expense associated with the changeover can easily be $400,000 to $800,000 or more for a large hospital. Further, it typically takes a hospital several years to fully implement bar-coded forms throughout the hospital. During that interim time period, the electronic capture of patient charts is either implemented at significant expense (since the records do not uniformly include bar-codes) or not implemented until a high percentage of the forms include bar codes. Another impediment to the implementation of bar-coded forms is the common administrative requirements for approving changes to forms, which are time-consuming and difficult to achieve. Still further, revision of pre-printed forms or software programs that generate forms can be cost-prohibitive for most organizations.

In these respects, the intelligent medical chart capture system according to the present invention permits a healthcare facility or health care system to implement a reliable electronic medical chart capture and recognition system without having to resort to manually separating and classifying by type the documents in the chart, and without requiring the revision of health care forms (such as by the inclusion of bar codes).

SUMMARY OF THE INVENTION

In view of the foregoing disadvantages inherent in the known types of document scanning and retention systems now present in the prior art, the present invention provides a new intelligent medical chart capture system wherein the same can be utilized for scanning medical charts and discriminating between the size and type of documents in the medical chart without needing to manually separate and classify by type the documents in the chart.

To attain this, the present invention generally comprises a method of capturing and processing medical charts of a health care facility. The method may include building a document capture template for types of documents used by the health care facility, and then forming a batch of medical charts that includes at least one medical chart, with each medical chart including at least one document and each document including at least one page, and with the pages of the medical chart being undivided from each other. The method may further include scanning the pages of the batch of medical charts and recognizing characters of text marked on the pages of the medical charts of the batch. The method may also include analyzing the text of the pages of the medical charts of the batch using the document capture template, dividing the scanned pages into at least two documents, and assigning a document type to each of the at least two documents. The method may then further include creating an index of the pages using the document types assigned to each of the at least two documents.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The system of the invention provides a method and apparatus for automatically capturing and discriminating the size and type of documents in the medical chart, without requiring manual separation and labeling (such as with a bar code) of each document of the medical chart prior to scanning, and without requiring the implementation of new forms to facilitate document discrimination. Further, since classification of the documents is based upon the content of the document, and not, for example, the appearance of the document, making changes in standardized forms that may make up the documents are more easily accommodated.

Further advantages of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects of the invention will become apparent when consideration is given to the following detailed description thereof. Such description makes reference to the annexed drawings wherein.

DESCRIPTION OF PREFERRED EMBODIMENTS

Figure 1:
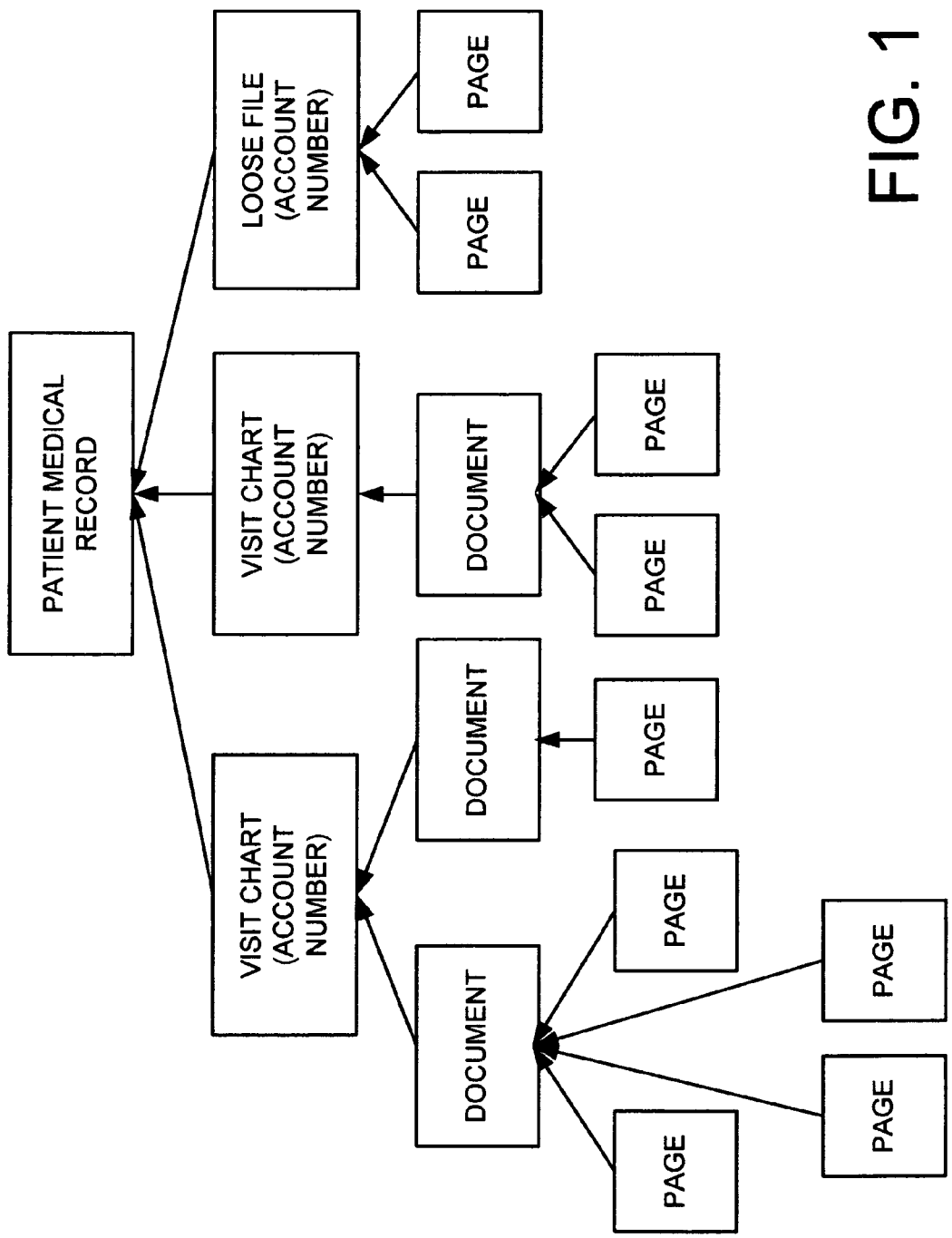
FIG. 1 is a schematic diagrammatic representation of a typical medical record of a patient.
Figure 2:
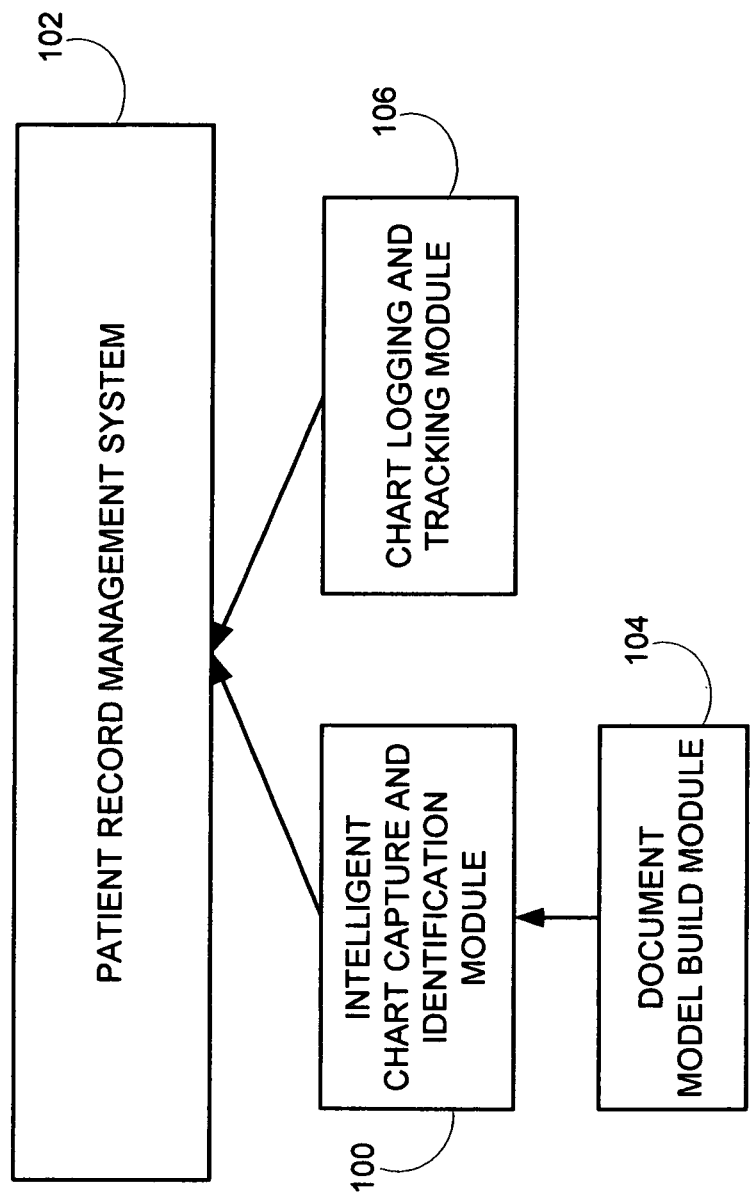
FIG. 2 is a schematic diagrammatic representation of the broad elements of a new intelligent medical chart capture system according to the present invention

With reference now to the drawings, and in particular to FIGS. 1 through 12 thereof, a new intelligent medical chart capture system embodying the principles and concepts of the present invention and generally designated by the reference numeral 10 will be described.

For the purpose of clarity in this description, a number of the terms that are used in the description will be defined and explained. As used herein, the terms "medical chart", "patient chart", and "chart" refer to the paper medical record for a specified visit for a patient at a health care facility or organization. A patient's "medical record" is defined in these terms as a collection of one or more of the patient's charts combined together (see, for example, FIG. 1). The term "loose file" refers to a single document from a paper chart that is brought down for scanning independent of any other documents that may be contained in a patient's medical chart. The term "document" refers to one or more pages that constitute a single form in a chart for a health care organization and/or that are typically indexed together (e.g., in one file) as a single entry in a health care document management system. The term "form" is used interchangeably with "document" in the following description, but is intended to also describe documents with a more formalized format that may be used consistently through a health care facility. The term "document type" refers to the type or category that a document falls into, and may be how the document is characterized in an index of the medical chart. Some examples of document types are, for example, lab report, MRI or CT scan result, a radiology report, physician's orders, subjective history, objective history, pharmacist's report, therapy plan of care, discharge summary, etc.

The term "document management system" refers to the electronic database and storage system in which patient charts are stored after scanning and processing to permit later electronic retrieval. The terms "indexing" and "indexed" as used in this description refer to the methodology for associating patient demographic information with the documents in the document management system. The term "patient account number" refers to the health care organization's tracking number for a specific visit by a patient to the health care facility, and thus the patient account number may also correspond to a particular patient medical chart.

The term "intelligent chart capture" process refers to the process and underlying customized software used within the overall capture and storage process to efficiently classify health care documents accurately and with minimal human intervention. The term "document model build" process refers to the process and underlying customized software used within the overall capture and storage process to create the customized software configuration for a health care organization that recognizes the particular health care forms utilized in that organization through optical character recognition and associates the forms with document types used in the document management system. The document model build process creates a "document model" that includes information about the characteristics of various types of documents and rules regarding discriminating between pages and documents based upon the characteristics of the document types. The document model may include one or more capture templates. The term "template" or "capture template" refers to information about documents, such as rules directed to recognizing document types, that is at least partially customized for the documents employed in one or more particular health care facilities providing the charts to be captured. The term "chart logging and tracking" process refers to the process and underlying customized software used to log the progress of a medical chart in the scanning, indexing and release process of the intelligent chart capture process. The term "release" refers to the process of transferring classification of documents and the associated images to the document management system and relating the information to patient demographics already existing in the document management system's database, and when the scanning and processing of the chart, or batch of charts, is considered to be complete.

In general, the overall intelligent medical chart capture system 100 of the invention comprises processes with automated steps for capturing charts as well as some steps performed by humans. The steps performed by humans are minimized compared to prior known chart capture processes and the automated steps are emphasized and expended through the use of optical character recognition-based software that analyzes the content recognized in the pages of the chart to discriminate between discrete documents in the chart, and also identifies the type of document after it has been discriminated from other documents in the chart. As illustratively shown in FIG. 2, the system 100 may be implemented as a module on a patient record management system 102 and may utilize a document model build module 104 for obtaining information about the various document types and creating rules to be applied to the content of scanned documents to determine the types and boundaries of the documents in a group of pages. A chart logging and tracking module 106 may also be implemented on the record management system 102 for managing data regarding the scanned documents including information about the scanning process (e.g., batch scanning information) and information about the indexing of the documents.

Figure 4:
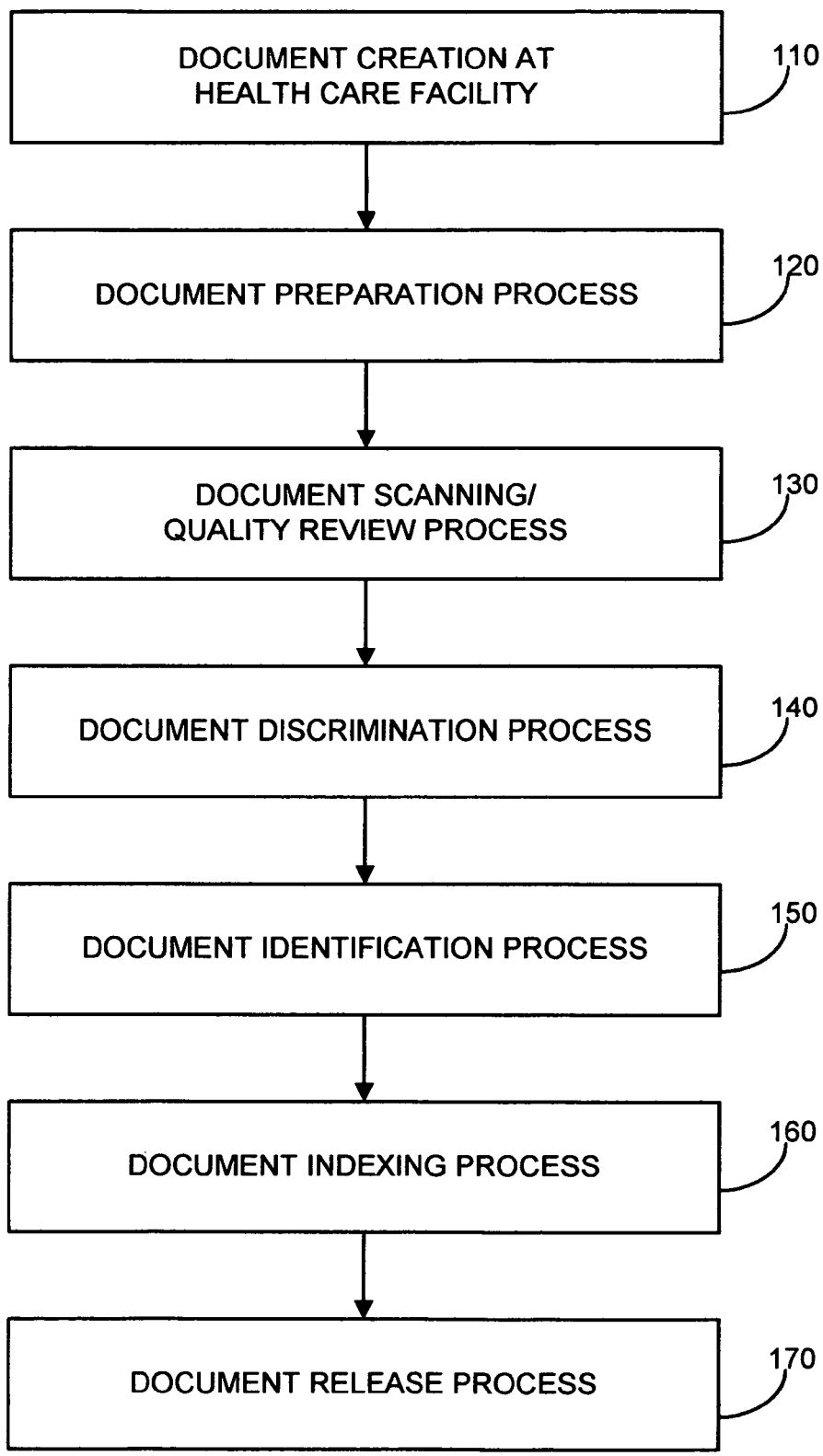
FIG. 4 is a schematic flow diagram of one portion of a process of the present invention.
Figure 5:
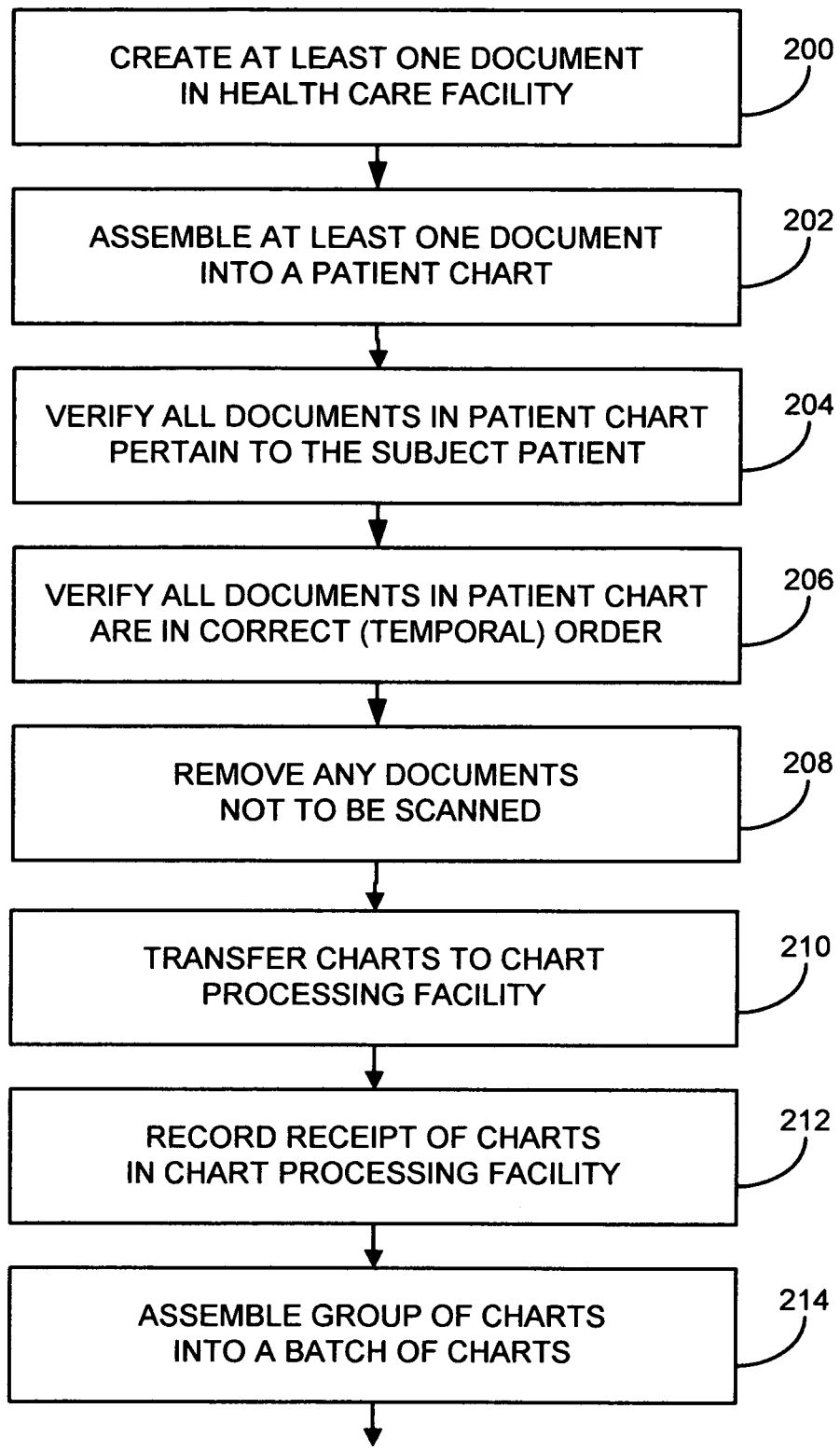
FIG. 5 is a schematic flow diagram of another portion of the process of the present invention.

In somewhat greater detail, and as illustratively shown in FIG. 4, the intelligent medical chart capture system 100 follows the creation of the documents that form the medical chart at the health care facility (110). The chart or document preparation process (120) involves the review of the chart for problems that should be resolved prior to the scanning and capture of the chart, and may also be performed at the health care facility prior to transfer of the chart to the facility providing the chart scanning and capture. The system 100 may include a process (130) for scanning the papers of the documents into the system, and performing a quality review for the scanning, and a process (140) for discriminating between the individual documents of the chart, and a process (150) for identifying the type of document. The system 100 may also include a document indexing process (160) for indexing the captured documents stored in the database for retrieval, and may also include a document release process (170). It will be apparent to those skilled in the art that some of the processes set forth above may be omitted.

In still greater detail, and as shown in FIGS. 5 through 11, preliminary to the application of the system 100 of the invention to the medical chart, a number of steps may be taken with respect to the medical chart to ensure the integrity of the chart, and these steps may be taken at the health care facility or off site from the health care facility. In these preliminary steps, shown in FIG. 5, at least one document may be created (200) in a health care facility pertaining to a patient's particular visit to the heat care facility, and the document may be assembled (202) into a medical chart with other documents pertaining to the patient's visit to the health care facility. Verification (204) that all documents in the patient chart pertain to the subject patient may be performed, and verification (206) that all documents in the patient chart are in correct (temporal) order may also be performed. Further, any documents not to be scanned into the record management system 102 may be removed (208) from the chart. It should be recognized that the preceding steps may or may not be included in the system of the invention, and thus may or may not be provided by a service provider utilizing the system.

Figure 6:
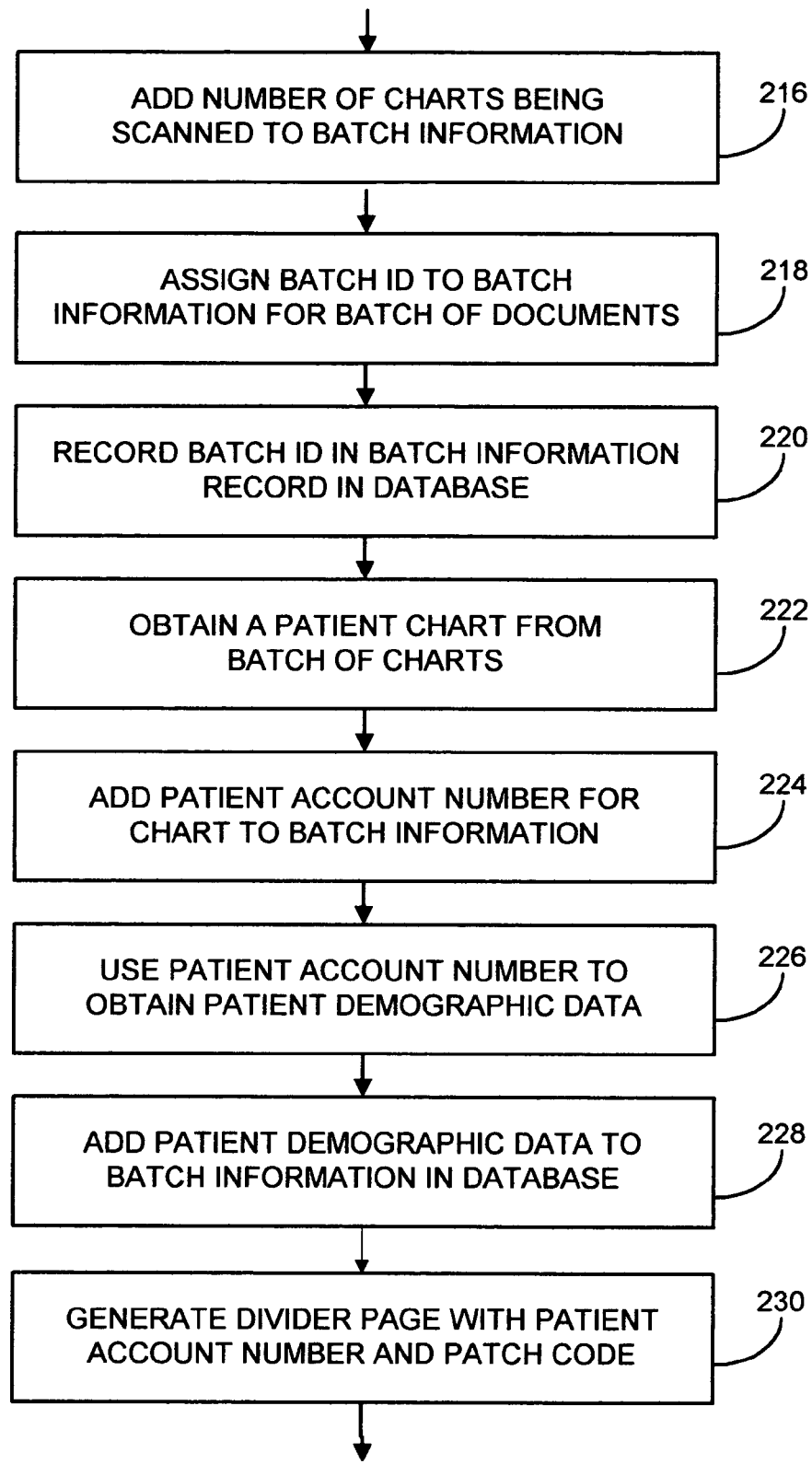
FIG. 6 is a schematic flow diagram of another portion of the process of the present invention.

The medical charts may then be transferred (210) to the chart processing facility if the location of the facility is different than the health care facility. The receipt of charts received at the chart processing facility may be recorded (212) in a database that may be a part of the chart logging and tracking module 106 of the patient record management system. A quantity of the charts may be segregated from other charts and assembled (214) into a batch for handling as a group in the processing facility. The batch may include the charts of a number of different patients, as well as loose documents that are not a part of a complete medical chart. As shown in FIG. 6, the number of charts in the batch to be scanned may be added (216) to the batch information. A batch identification (ID) may be assigned (218) to the batch of charts being processed, and the batch ID may be recorded (220) in a batch information record in the database of the chart logging and tracking module 106. A patient chart may then be obtained (222) from the batch of charts, and a patient account number may be added (224) to the batch information in the database. The patient account number may then be used (226) to obtain or call up the patient's demographic data from the health care facility's data that may be provided with the charts, and the patient's demographic data may be added (228) to the batch information in database. A divider page (230) may be generated with the patient account number as well as other pertinent information.

Figure 7:
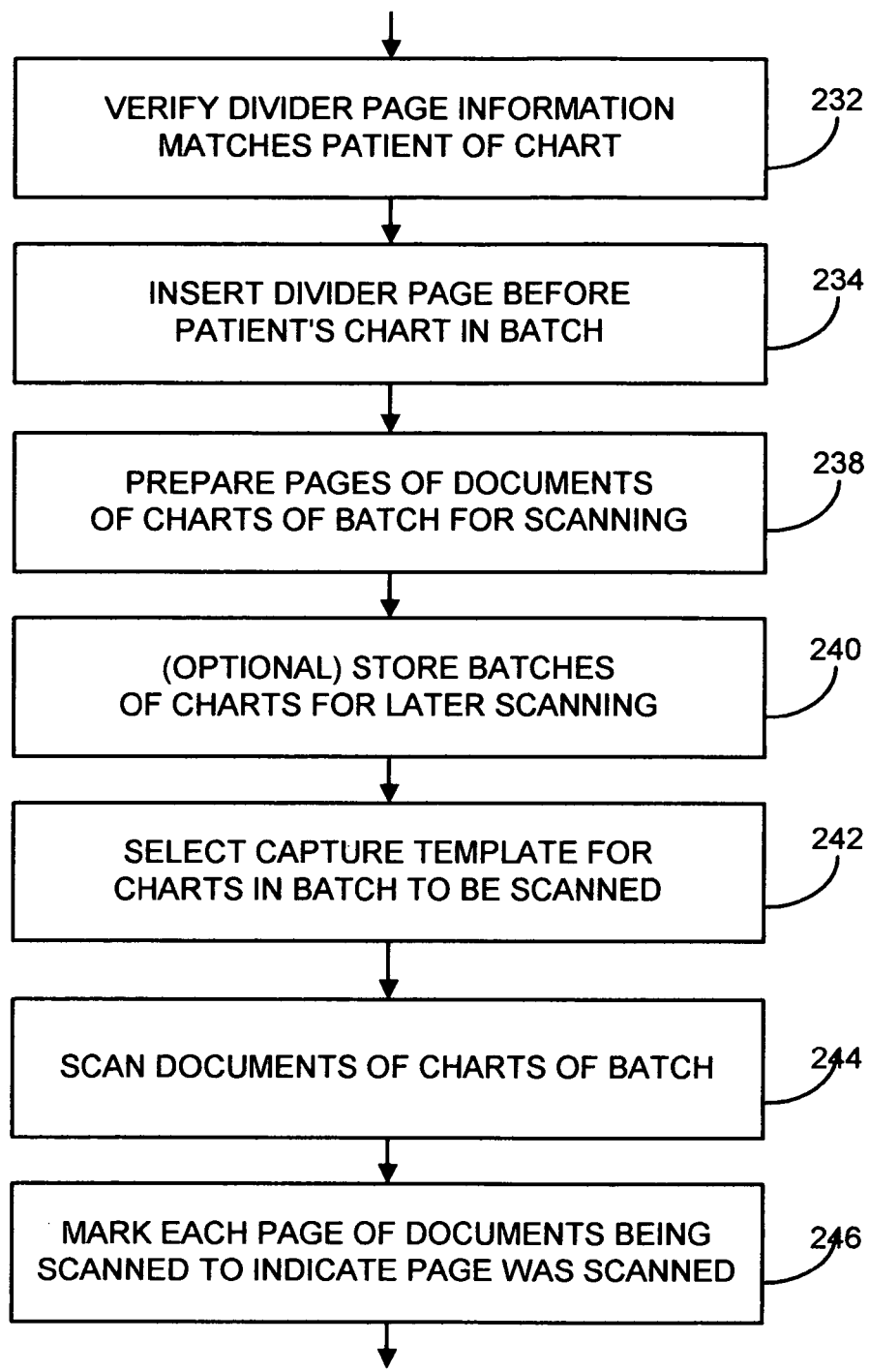
FIG. 7 is a schematic flow diagram of another portion of the process of the present invention.
Figure 8:
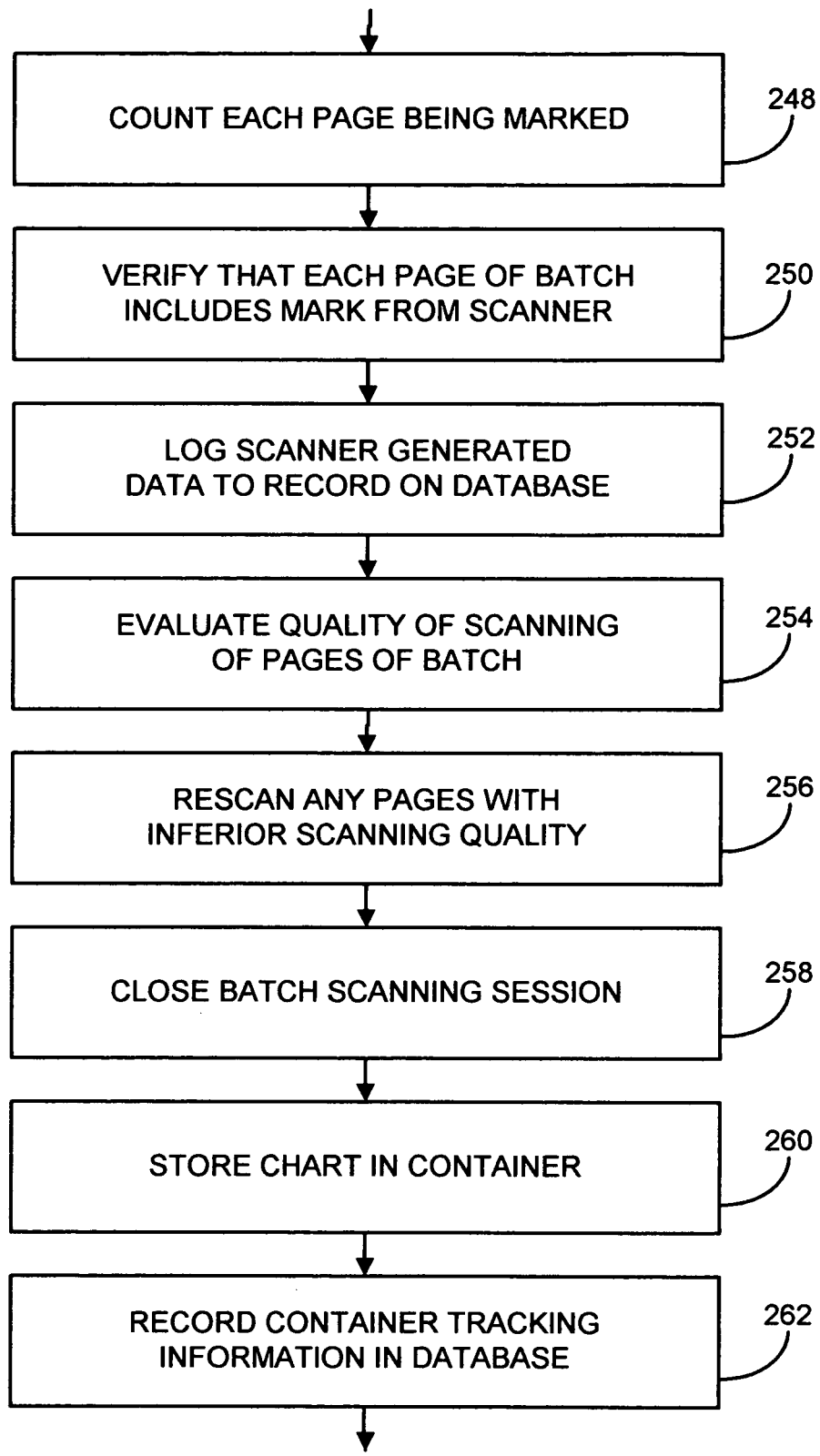
FIG. 8 is a schematic flow diagram of another portion of the process of the present invention.

Continuing with FIG. 7, the information on the divider page is compared to the information on the patient medical chart to verify (232) that the divider page matches the patient of the medical chart of the batch. The divider page may be inserted (234) into the batch before the patient's medical chart to signify the end of the previous chart and indicate the beginning of a new medical chart. The operator than may prepare (238) the pages of the documents of the medical charts of the batch for the scanning operation, such as by removing any staples or other impediments to scanning the pages. Optionally, the batch or batches prepared by the operator may be set aside or stored (240) for a scanning operation at a later time. The operator may then select (242) a capture template that is appropriate for the particular medical chart that is being included in the batch. The capture template may be directed to the documents of the charts of one or more particular health care facilities or even departments of a health care facility. The scanning operation is then commenced to scan (244) the documents of the charts of the batch. As each page moves through the scanning apparatus, the page is marked (246) to provide a positive indication that the page was indeed scanned.

The module that performs the page image scanning function is most preferably a batch-oriented capture application designed to process (capture) large numbers of documents and forms with a high throughput in the scanning process, although other applications with lesser performance may be used. One suitable software program for performing the scanning capture of the pages of the documents of the charts is available under the tradename Kofax Ascent Capture V7 from Kofax Image Products of 16245 Laguna Canyon Road, Irvine, Calif. 92618-3603.

Once the scanning operation has been completed, the operator may then count (248) each page that has been marked to verify that each of the pages of the batch has been marked by the scanner as being scanned. The operator then verifies (250) that each page of batch includes a mark from the scanner. When the count has been verified and it is confirmed that each page of the batch has been scanned, the operator may log (252) the data generated by the scanner to a record in the database. The quality of the scanning of the pages of the batch may then evaluated (254), such as by the operator visually evaluating the quality of the images of the pages as presented on a screen. Any pages with inferior scanning quality may be rescanned (256) by the operator to insert into the record in place of any pages that may have been unfocused or shifted. When all pages are determined to be of acceptable quality, the batch scanning session may be closed (258). The chart may then be placed into storage, such as by storing (260) the chart in a container that includes a designation. The designation on the container may then be recorded (262) as container-tracking information in the database. At this point, handling of the physical or paper file of the medical charts may be discontinued, and further steps may be performed on the electronic version or form of the medical charts without requiring further reference to the paper chart.

Figure 9:
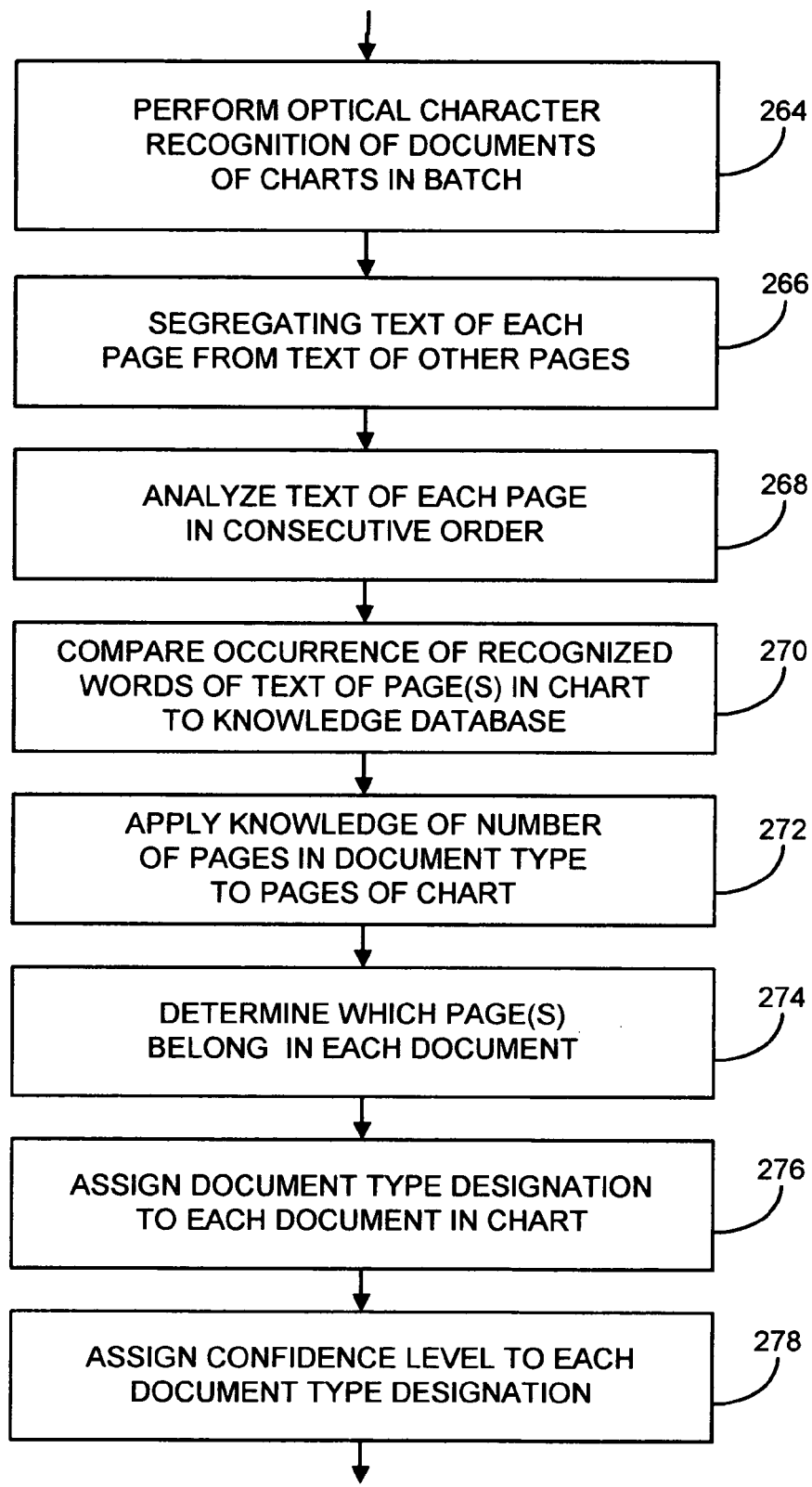
FIG. 9 is a schematic flow diagram of another portion of the process of the present invention.

Continuing with FIG. 9, the system performs (264) an optical character recognition (OCR) process on the pages of the documents of the charts in the batch that attempts to capture the verbal content of the pages by, for example, distinguishing the characters, including letters and numbers, in the document and providing that information as text data. The text data recognized from the images of the pages is segregated (266) according to the particular page on which it appears so that not only the type of the document can be determined, but also the particular pages making up that document can be discerned. The module providing the OCR function is preferably a software application that provides advanced document classification, separation, and extraction capabilities, enabling the automated processing of documents in a batch form, typically without requiring any dedicated computer indicia (such as bar codes) marked on the documents for the primary purpose of indicating the type and extent of the documents. One suitable software product for performing this function is available under the tradename of the Indicius Module of the Kofax Ascent Capture software product from Kofax Image Products of 16245 Laguna Canyon Road, Irvine, Calif. 92618-3603.

Once the text on the pages of the chart have been recognized and the page has thus been converted from image data to text data, the system then analyzes (268) the text data of each page in the consecutive order of the pages of the chart, and compares (270) the occurrence of the recognized words of the text of the pages in the chart to the information in the appropriate capture template, which includes various rules for determining the type of document based upon the occurrence of various words in the text data from the page. The system applies (272) the rules to the text taken from each page of the chart. The system determines (274) which page(s) belong together as a discrete document of the chart, and based upon that determination may create associations between two or more pages that indicate that the pages comprise a distinct document. In this manner, pages of the initial group of individual pages of the chart are logically associated with other pages of the group to form pages of one or more documents, and the pages of one document are logically separated from the pages of the other documents of the chart. Once the pages have been logically divided into individual documents, the system then assigns (276) a designation of a document type to each of the documents in the chart based upon the text contained in the document. This designation of document type is preliminary, and may be changed as described below, and if not changed will become final. The system may also assign (278) a level of confidence score to each document type designation for the documents of the chart. The level of confidence may be based upon the degree to which the text contained in the document matches or agrees with words or terms associated with the document type in the knowledge database. Once the pages of the medical chart have been segregated into documents and a document type has been assigned to the documents, the text data does not need to be retained for further use, although it is not necessary that the text data be destroyed.

Figure 3:
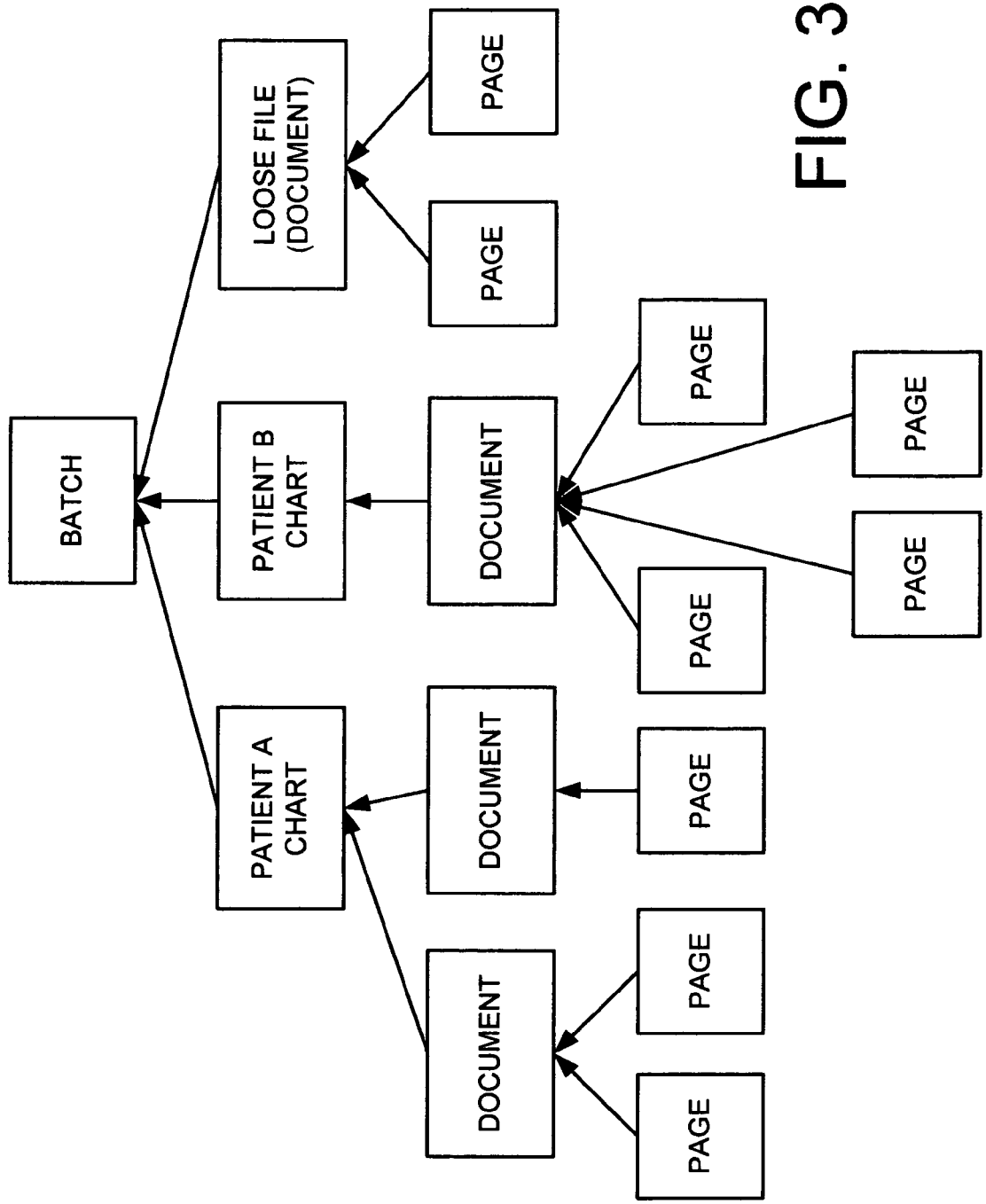
FIG. 3 is a schematic diagrammatic representation of an illustrative make up of a batch of medical charts for scanning and classifying by the present invention.
Figure 10:
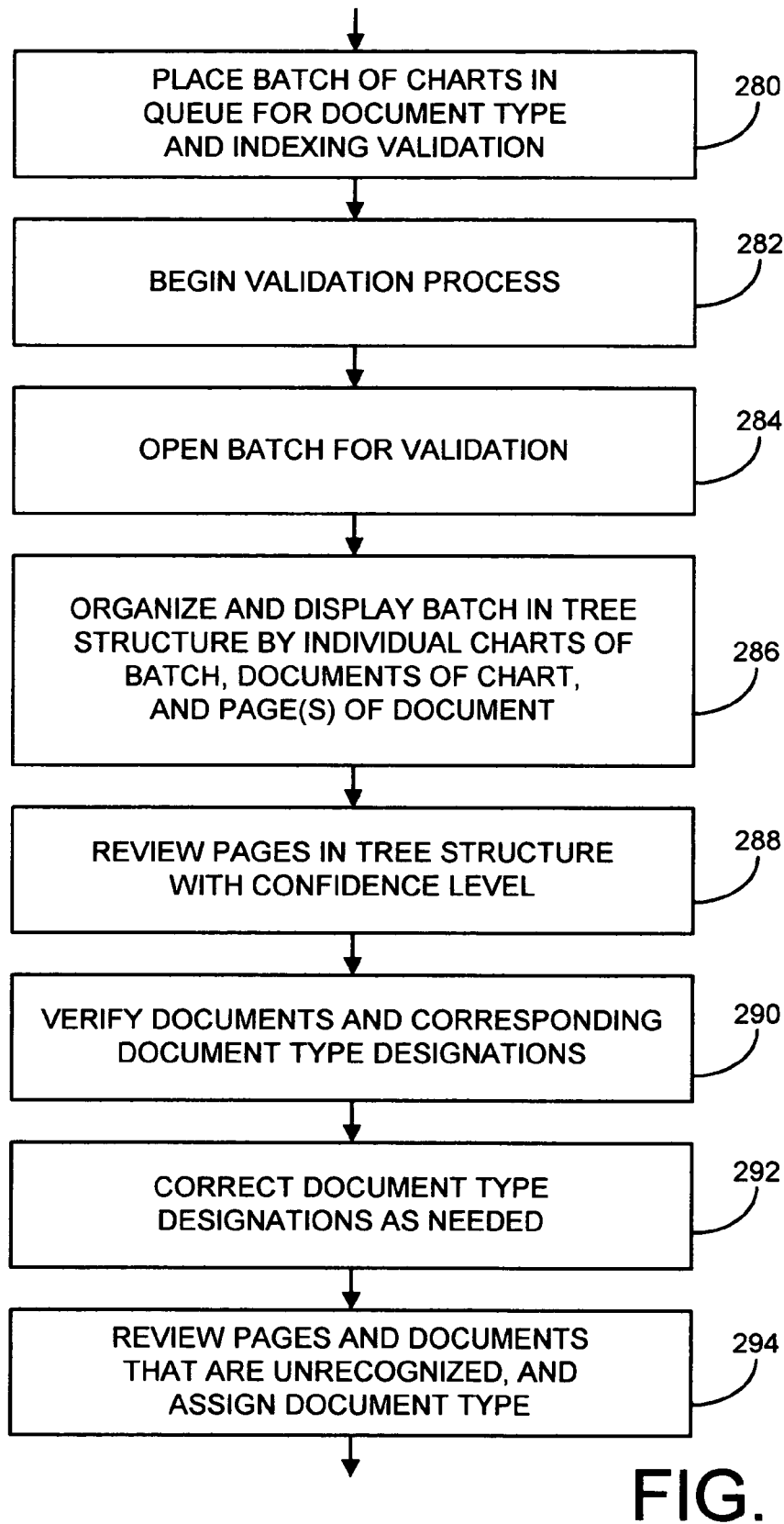
FIG. 10 is a schematic flow diagram of another portion of the process of the present invention.

Continuing with FIG. 10, the operator may place (280) the electronic file for the scanned batch of medical charts in a queue for validation of the document type and indexing that has been assigned by the system to the documents of the charts of the batch. When the file of the scanned batch comes up in the validation queue, the validation process is begun (282). The electronic file for the batch is opened (284), and the individual charts of the batch, the documents of the chart (s), and the page(s) of the documents may be organized and displayed (286) in tree structure for review by a quality review personnel (such as is schematically shown in FIG. 3). The confidence level of the system for the particular document-type designation assigned to each document may also be displayed with the respective document for viewing by the quality review person or technician. The quality review technician may review (288) the pages of the documents in the tree structure format with the assigned confidence level, typically by visually looking at the papers of the documents. The quality review technician verifies (290) that the document type assigned by the system is accurate and represents the actual document type of the document. The quality review technician may review the document type designation for all of the documents of the charts of the batch, or a portion of the documents of the charts of the batch. The portion of the charts reviewed may comprise those documents for which the system has assigned a relatively lower confidence level as compared to other documents of the batch of charts. If inaccurate document-type designations are discovered by the technician, he or she may correct (292) the document type designations for the affected document as required. Changes to document type designations made by the technician during the review may be logged for further analysis and refinement of the document model. The quality review technician may also review (294) the pages and the documents that were not recognized, or assigned a document type designation, by the system.

Figure 11:
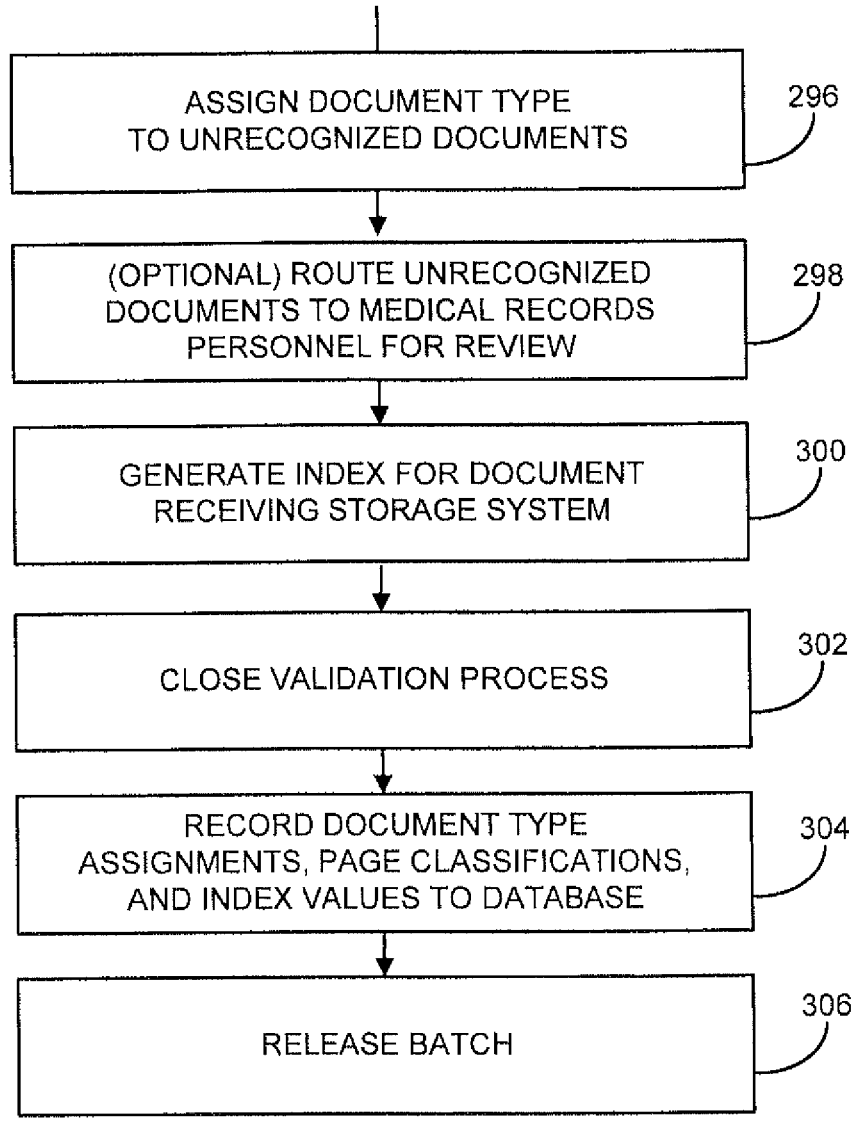
FIG. 11 is a schematic flow diagram of another portion of the process of the present invention.

Continuing on to FIG. 11, the quality review technician may assign (296) a document type to the unrecognized or unidentified document. Further, the technician may shift one or more pages between the documents if the page(s) have been incorrectly associated with other pages into a document. For example, if a page has been grouped with pages of a first document (such as the last page of the first document), but should have been grouped with pages of a second, subsequent document in the medical chart (such as the first page of the second document), then the technician may reassign the page from the first document to the second document.

Optionally, the quality review technician may route (298) a copy of the unrecognized document or documents from the batch to medical records personnel for reviewing the documents to help establish a new document type for the type of document if the document type does not exist in the system, or to adjust the system template to recognize the document as being of a particular document type if the document type is already a part of the template. This step may be a part of an ongoing adjustment and fine-tuning of the template employed to separate and identify documents by the system. It may also be suitable to rebuild the document model to include the manually-typed documents when, for example, it is noted that documents are not being identified, or are being misidentified, at a rate that is higher than a particular threshold.

The system may generate (300) an index of each document of the medical chart for each of the charts in the batch, and the index may be stored on the chart logging and tracking module 106. The validation process may then be closed (302), and the document type assignments, page classifications, and the indexing values may be recorded (304) on the database of the chart logging and tracking module for future reference in accessing the medical charts of the batch. The indexing values for the chart may include, for example, an identification or other location identifier that indicates the location of the object (the image of the referenced document) on the database for future retrieval. The batch may then be released (306), signifying that the processing and classification of the medical charts of the batch has been completed and the medical charts are available to be accessed by personnel.

Figure 12:
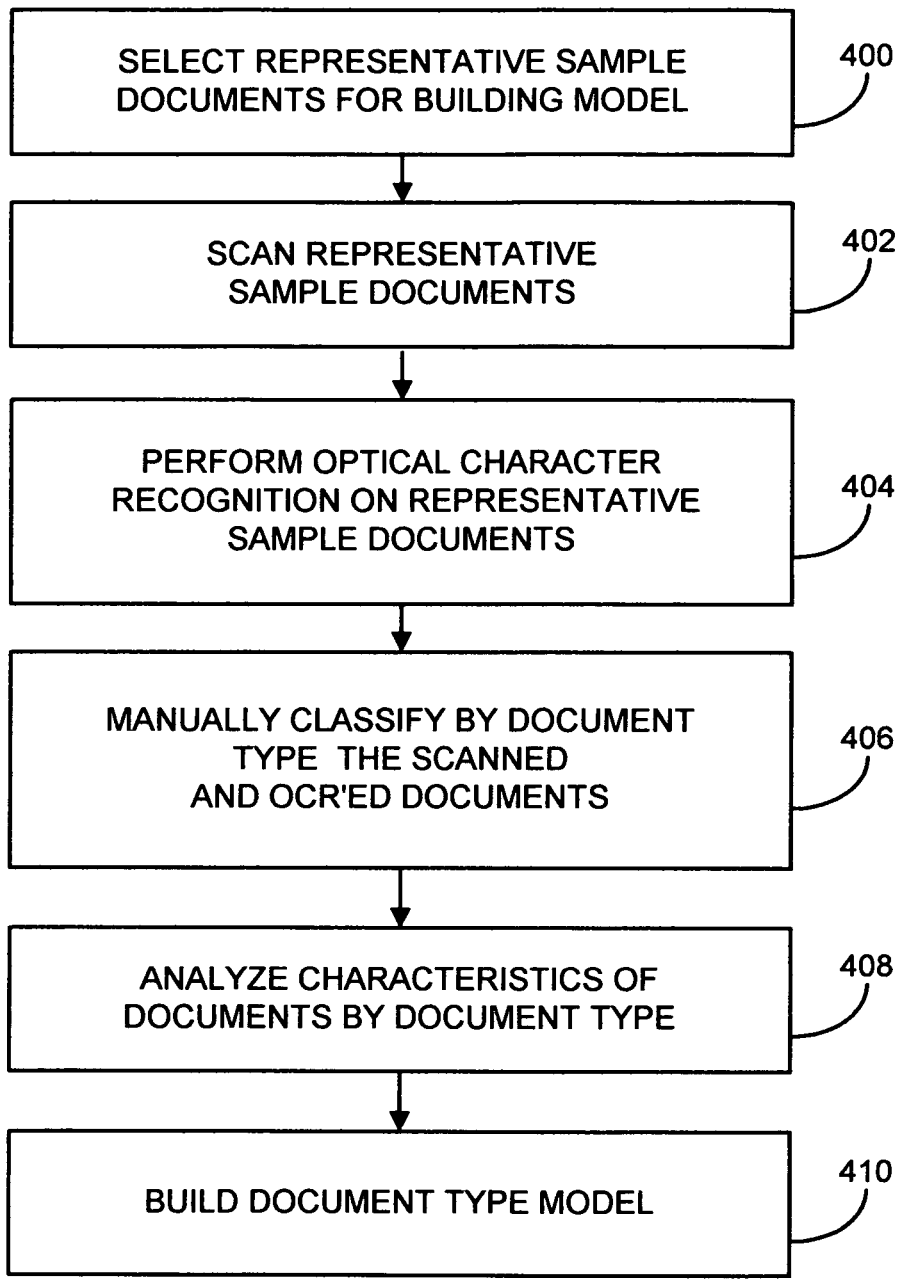
FIG. 12 is a schematic flow diagram of a model building process of the present invention.

Referring now to FIG. 12, a document model building process for training or set up of the system is depicted for initially allowing the system to develop one or more capture templates to facilitate the differentiation between, and recognition of, the documents and forms used in a particular health care facility, especially as they might differ from documents and forms used in other health care facilities. As each health care facility will use at least some documents and forms that differ from other health care facilities, as well as form department to department within the same health care facility, it is important to provide the system with a representative sample of the documents and forms that may be used in the facility to permit the system to analyze the pertinent verbal characteristics of the different documents so that a model may be developed based upon the characteristics detected. The differences in documents make it typically necessary to employ a model building process for each new facility in which the system is utilized in order to obtain the most accurate results in the analysis process.

As a part of the model building process, a representative sample of the documents utilized by the health care facility is selected (400) for building the document model, which preferably includes at least one example of each of the types of documents (e.g., forms) that are known to be used by the personnel of the health care facility in creating medical charts. Optionally, the documents may be segregated or distinguished by different departments of divisions of the health care facility, so that templates for the different departments may be constructed, if desired. The representative sample documents are then scanned (402), and optical character recognition is performed (404) on the scanned images of the sample documents. The documents of the various document types are then manually classified (406) by a person who identifies and inputs a particular document type for each of the documents that have been entered into the system during the document model build process. The document model build module 106 of the system then analyzes (408) the characteristics of the entered documents in light of the manually-indicated document type that has been associated with the document. The model build module of the system then builds (410) a model of the various document types based upon the terms and usage employed in the documents representative of the different types.

It should be recognized that the model building process may be repeated after the initial building process has occurred, such as upon the determination that the system is misclassifying or failing to classify the type of more than an acceptable number of the documents, or when a significant change is being made to the character of the documents being analyzed (for example, the implementation of new forms by the health care facility), or even upon the passage of a predetermined time interval between builds.

With respect to the above description then, it is to be realized that the optimum dimensional relationships for the parts of the invention, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A method of capturing and processing medical charts of a health care facility absent pre-printed identifying indicia implemented on a computerized document scanning system, the method comprising:

building, by at least one computer in a set of one or more computers, an electronic document capture template for types of documents used by the health care facility, wherein the building includes the steps of:
providing a representative sample of a plurality of documents utilized in a health care facility, each of the documents representing at least one type of document utilized in the health care facility, each of the documents having text marked thereon;
scanning the plurality of documents of the representative sample;
analyzing, by said at least one computer in a set of one or more computers, text from the plurality of documents with an indicated document type for the document; and
forming, by said at least one computer in a set of one or more computers, the document capture template for the documents of the health care facility comprising the rules for the types of documents;
forming a batch of medical charts including at least one medical chart, each medical chart including at least one document, each document including at least one page, the pages of the medical chart being undivided from each other, wherein each document is free of any non-text encoded indicia indicating a document form;
scanning the pages of the batch of medical charts using an image scanner;
recognizing, by said at least one computer in a set of one or more computers connected to said image scanner, characters of text marked on the pages of the medical charts of the batch analyzing, by said at least one computer in a set of one or more computers, the recognized characters of text on said computer using the document capture template using said computer;

dividing, by said at least one computer in a set of one or more computers, the scanned pages into at least two documents based on the recognized characters of text and the document capture template using said computer;

assigning, by said at least one computer in a set of one or more computers, a document type, after said scanning, to each of the at least two documents based upon the recognized characters of text and the document capture template;

determining, by said at least one computer in a set of one or more computers, a confidence level of the assignment of the document type to the at least two documents;

storing, by said at least one computer in a set of one or more computers, said at least two documents in an electronic database connected to said computer; and creating, by said at least one computer in a set of one or more computers, an electronic index of the pages using the document types assigned to each of the at least two documents.

2. The method of claim 1 further comprising reviewing the scanned pages of the at least two documents for accuracy of the division of the scanned pages into the at least two documents.

3. The method of claim 1 further comprising reviewing the scanned pages of the at least two documents for accuracy of the assignment of the document type to each of the at least two documents.

4. The method of claim 3 further comprising displaying the pages of the batch for visual review of the pages.

5. The method of claim 1 wherein analyzing including applying rules regarding occurrence of text on the scanned pages.

6. The method of claim 1 wherein the analyzing step further comprises:

recognizing characters of the text marked on each of the plurality of documents;

determining patterns in the text marked on each type of document; and creating a rule for each type of document in the representative sample.

* * * * *